US012605203B2

(12) United States Patent
Xu et al.

(10) Patent No.: US 12,605,203 B2
(45) Date of Patent: Apr. 21, 2026

(54) MICROWAVE ABLATION ELECTRODE

(71) Applicant: MIANYANG LIDE ELECTRONICS CO., LTD., Mianyang (CN)

(72) Inventors: Dong Xu, Mianyang (CN); Hu Liao, Mianyang (CN); Gang Dong, Mianyang (CN); Liang Liang, Mianyang (CN); Yingxia Zhang, Mianyang (CN); Yongsheng Li, Mianyang (CN); Xiaofang Wang, Mianyang (CN)

(73) Assignee: MIANYANG LIDE ELECTRONICS CO., LTD., Mianyang (CN)

( * ) Notice: Subject to any disclaimer, the term of this patent is extended or adjusted under 35 U.S.C. 154(b) by 0 days.

(21) Appl. No.: 18/550,471

(22) PCT Filed: May 18, 2023

(86) PCT No.: PCT/CN2023/094993
§ 371 (c)(1),
(2) Date: Sep. 14, 2023

(87) PCT Pub. No.: WO2024/216697
PCT Pub. Date: Oct. 24, 2024

(65) Prior Publication Data
US 2026/0026880 A1     Jan. 29, 2026

(30) Foreign Application Priority Data
Apr. 19, 2023     (CN) .......................... 202310418825.4

(51) Int. Cl.
*A61B 18/18*     (2006.01)
*A61B 18/00*     (2006.01)

(52) U.S. Cl.
CPC ... *A61B 18/1815* (2013.01); *A61B 2018/00023* (2013.01); *A61B 2018/00577* (2013.01);
(Continued)

(58) Field of Classification Search
CPC ............................ A61B 18/18; A61B 18/1815
See application file for complete search history.

(56) References Cited

U.S. PATENT DOCUMENTS 8,932,281  B2 *   1/2015   Brannan   ............  A61B 18/1815
                                                                606/41
2007/0203551  A1 *   8/2007   Cronin   ...................  A61B 18/04
                                                                607/101

(Continued)

*Primary Examiner* — Ronald Hupczey, Jr.
(74) *Attorney, Agent, or Firm* — Nelson Mullins Riley & Scarborough LLP

(57)          ABSTRACT

A microwave ablation electrode is provided. The microwave ablation electrode mainly comprises a main needle body. A working end of the main needle body can release microwave energy to realize microwave ablation. A non-working end circulation cooling structure and a working end liquid injection structure are arranged on the main needle body, wherein the non-working end circulation cooling structure can allow a refrigerant medium to reach a front end of a non-working end of the main needle body to cool the non-working end of the main needle body and the surrounding tissues, and the non-working end circulation cooling structure can allow the refrigerant medium to flow back. The working end liquid injection structure can allow the refrigerant medium to reach the working end of the main needle body to cool the working end and the surrounding tissues.

6 Claims, 4 Drawing Sheets

(52) U.S. Cl.
CPC ................. *A61B 2018/1853* (2013.01); *A61B 2018/1869* (2013.01); *A61B 2018/1892* (2013.01)

(56) References Cited

U.S. PATENT DOCUMENTS

| | | | |
|---|---|---|---|
| 2016/0081748 A1* | 3/2016 | Paulus | ................... A61B 18/18 606/33 |
| 2020/0188021 A1* | 6/2020 | Wong | ..................... A61B 34/30 |

* cited by examiner

MICROWAVE ABLATION ELECTRODE

CROSS-REFERENCE TO RELATED APPLICATIONS

This patent application claims priority to and is a 35 U.S.C. § 371 U.S. is a National Stage Application of International Patent Application No. PCT/CN2023/094993, entitled "Microwave Ablation Electrode", filed on May 18, 2023, which claims the benefit and priority of Chinese Patent Application No. 202310418825.4 filed on Apr. 19, 2023, the disclosure of each being incorporated by reference herein in their entireties.

TECHNICAL FIELD

The present disclosure relates to the technical field of medical appliances, in particular to a microwave ablation electrode.

BACKGROUND

Microwave ablation is a mature and commonly used ablation method. Microwave ablation is mainly used for the treatment of nodules, tumors in tissues and organs and other diseases of the human body, mainly relying on the friction and collision of polar molecules (water molecules) in a microwave field to generate heat, and the thermal effect causes protein denaturation and coagulation of cancer cells, leading to irreversible necrosis, thus killing tumor cells. Microwave ablation therapy is involves puncturing a working end of an ablation electrode into lesion parts and releasing microwave energy, so that the temperature of cells at the lesion parts is increased, the cells are denatured, and finally the tissues at the lesion parts are necrotic and can be absorbed and removed through normal metabolism and absorption of the human body, so that the purpose of eliminating nodules and tumors is achieved.

Microwave radiates energy to a surrounding space after being emitted from a microwave generator, and part of the energy can cause temperature rise after passing through a coaxial semi-rigid wire and the working end of the electrode. Therefore, most of conventional microwave ablation electrodes are provided with an internal cold circulation structure. As shown in FIG. 1, an existing microwave ablation electrode is usually of a half-needle cold circulation structure, that is, a cold circulation structure is arranged behind the reflecting ring 110, and can only cool the coaxial semi-rigid wire behind the reflecting ring 110, but cannot cool the working end part of the ceramic needle body 102, and even cannot cool the tissues around the working end.

However, the principle of microwave ablation determines that a transmitting antenna at the working end itself will generate heat, especially after the tissues near the working end are carbonized and dehydrated and the characteristic impedance is changed, and the microwave transmitting end will generate heat seriously. The working end of the microwave ablation electrode is usually made of ceramic, the outer needle tube is mostly made of metal material, and the working end of the microwave ablation electrode and the outer needle tube are usually connected by a sealing adhesive. When the transmitting antenna itself generates heat seriously, the sealing adhesive is easy to melt and the bonding strength is reduced. At the same time, high-temperature and high-pressure gas is generated inside the working end, so that the ceramic needle body falls off from the outer needle tube, and the ceramic needle body can even puncture other important parts under the action of high-pressure gas after falling off, so that great medical risks may be caused. Moreover, the concentration of microwave heat is easy to cause the carbonization of the tissues around the working end, continuous input of microwave energy is hindered, resulting in a small ablation range and an irregular ablation shape, and carbonized lesion tissues affect the healing effect.

SUMMARY

The present disclosure aims to provide a microwave ablation electrode to solve the problems in the prior art. Dual ablation of steam thermal ablation and microwave ablation is realized, the ablation effect is improved, the temperature of the working end of the microwave ablation electrode can be reduced, the wettability of the surrounding tissues at the working end can also be increased, and the carbonization of the lesion tissues is reduced.

In order to achieve the aim, the present disclosure provides the following solution.

The present disclosure provides a microwave ablation electrode, including a main needle body. A working end of the main needle body is capable of releasing microwave energy to realize microwave ablation. A non-working end circulation cooling structure and a working end liquid injection structure are arranged on the main needle body.

The non-working end circulation cooling structure is capable of allowing a refrigerant medium to reach a front end of a non-working end of the main needle body to cool the non-working end of the main needle body and the surrounding tissues, and the non-working end circulation cooling structure is capable of allowing the refrigerant medium to flow back.

The working end liquid injection structure is capable of allowing the refrigerant medium to reach the working end of the main needle body to cool the working end of the main needle body and the surrounding tissues, and is also capable of allowing the refrigerant medium to be injected into the lesion tissues and absorb microwave energy to form steam, so that steam thermal ablation is realized.

Preferably, the main needle body includes an inner needle tube, an outer needle tube, a reflecting ring, a coaxial semi-rigid wire and a working end needle body. The outer needle tube is sleeved on the inner needle tube. The inner needle tube is sleeved on the coaxial semi-rigid wire. The reflecting ring is sleeved on the coaxial semi-rigid wire. An inner wall of the reflecting ring is sealed with an outer wall of the coaxial semi-rigid wire. The reflecting ring is capable of sealing a front end of the inner needle tube. The working end needle body is arranged at a front end of the outer needle tube. A front end of the coaxial semi-rigid wire is electrically connected with a transmitting antenna, and a tail end of the coaxial semi-rigid wire is capable of being electrically connected with a microwave ablation host. The transmitting antenna is located in the working end needle body.

Communicating gaps are arranged between the transmitting antenna and an inner wall of the working end needle body and between the front end of the coaxial semi-rigid wire and the inner wall of the working end needle body to form a working end flow channel. The working end flow channel communicates with the non-working end circulation cooling structure. Micropores which allow the refrigerant medium to be injected into the lesion tissues are formed in the working end needle body. The micropores communicate with the working end flow channel to form the working end liquid injection structure.

Preferably, an inner flow channel is formed between the inner needle tube and the coaxial semi-rigid wire. An outer flow channel is formed between the outer needle tube and the inner needle tube. A front end of the inner flow channel communicates with a front end of the outer flow channel, and a tail end of the inner flow channel and a tail end of the outer flow channel communicate with a liquid outlet port and a liquid return port of a liquid supply device, respectively to form the non-working end circulation cooling structure, wherein the liquid supply device is capable of providing the refrigerant medium, and the outer flow channel communicates with the working end flow channel.

Preferably, a tail end of the main needle body is connected with a liquid cavity. A liquid inlet cavity and a liquid return cavity which are separated from each other are formed in the liquid cavity. The tail end of the inner flow channel and the tail end of the outer flow channel communicate with the liquid inlet cavity and the liquid return cavity, respectively. The liquid inlet cavity and the liquid return cavity are connected with the liquid outlet port and the liquid return port of the liquid supply device through a liquid inlet pipe and a liquid return pipe, respectively.

Preferably, a liquid amount adjusting device is installed on the liquid inlet pipe and/or the liquid return pipe, and the liquid amount adjusting device is used for adjusting the liquid inlet amount or the liquid return amount of the refrigerant medium so as to adjust the injection amount of the refrigerant medium, wherein the refrigerant medium is sterile physiological saline, sterile liquid for injection or liquid medicine, the injection amount of the refrigerant medium is the volume of the refrigerant medium entering the human body per unit time, and the injection amount of the refrigerant medium is 0.1 ml to 2.0 ml per minute.

Preferably, side holes are formed in a side face of the front end of the inner needle tube, and the inner flow channel communicates with the outer flow channel through the side holes.

Preferably, a first gap is arranged between an outer wall of the reflecting ring and an inner wall of the outer needle tube, and a second gap is arranged between a front end face of the reflecting ring and a tail end face of the working end needle body, wherein the first gap communicates with the outer flow channel, the second gap communicates with the working end flow channel, and the first gap communicates with the second gap to realize the communication between the working end flow channel and the outer flow channel.

The first gap has a spacing of 0.05 mm to 0.2 mm, and the second gap has a spacing of 0.1 mm to 1.0 mm.

Preferably, the outer needle tube is made of metal material, the outer needle tube is capable of being arranged in a grounded shield manner, and an anti-sticking insulation layer is arranged on an outer wall of the outer needle tube. An anti-sticking layer is arranged on an outer wall of the working end needle body, the anti-sticking layer is arranged in a staggered manner with the micropores, and the anti-sticking layer is flush with the anti-sticking insulation layer.

Preferably, the main needle body has a minimum diameter of 1.20 mm.

Preferably, the working end needle body includes a ceramic needle body and a ceramic needle tip, a tail end of the ceramic needle body is connected with the front end of the outer needle tube, the ceramic needle tip is arranged at a front end of the ceramic needle body, wherein the micropores are formed in the ceramic needle body, and a developing groove is formed in the ceramic needle tip.

Preferably, each of the micropores has a pore size of 50 μm to 200 μm.

Compared with the prior art, the present disclosure has the following technical effects.

The working end liquid injection structure is also arranged on the main needle body and can allow the refrigerant medium to reach the working end of the main needle body to cool the working end of the main needle body and the surrounding tissues, so that the working end temperature of the main needle body can be reduced, and the glue at the bonding place between the working end needle body and the outer needle tube is avoided from being melted at high temperature, causing the working end needle body to fall off. Moreover, in the present disclosure, the working end liquid injection structure can also allow the refrigerant medium to be injected into lesion tissues, so that the wettability of the surrounding tissues at the working end can be increased, the temperature of the surrounding tissues at the working end is reduced, the carbonization of the tissues is avoided, the characteristic impedance of the tissues is maintained for a long time, and the injection of microwave energy is facilitated. Therefore, the ablation range is expanded, and the ablation shape is more regular. In addition, during the process that the refrigerant medium enters the lesion tissues, the microwave energy is absorbed, high-temperature steam can be formed to realize steam thermal ablation, so that dual ablation of microwave ablation and steam thermal ablation is realized, and the ablation effect is improved. Further, the working end liquid injection structure can release high-pressure gas inside the working end while liquid is injected, so that the working end needle body is prevented from being broken under the action of high pressure, and the non-working end circulation cooling structure can also release the high-pressure gas.

Furthermore, the non-working end circulation cooling structure is also arranged on the main needle body, which can allow the refrigerant medium to cool the non-working end of the main needle body and the surrounding tissues, and can allow the refrigerant medium to flow back, so that high temperature of the non-working end of the main needle body is avoided from scalding normal tissues and damaging the coaxial semi-rigid wire, higher microwave power can be output, and the ablation efficiency is improved.

BRIEF DESCRIPTION OF THE DRAWINGS

To more clearly illustrate the present embodiment of the present disclosure or the technical scheme in the prior art, the following briefly introduces the attached figures to be used in the present embodiment. Apparently, the attached figures in the following description show merely some embodiments of the present disclosure, and those skilled in the art may still derive other drawings from these attached figures without creative efforts.

In FIG. 1: 101, ceramic needle tip; 102, ceramic needle body; 103, Teflon coating; 104, inner conductor; 105, insulating medium; 106, outer conductor; 107, outer needle tube; 108, inner needle tube; 109, round hole in inner needle tube; 110, reflecting ring; 111, sealing adhesive; 112, welding spot; and 113, transmitting antenna.

In the figures: 1, ceramic needle tip; 2, ceramic needle body; 3, transmitting antenna; 4, scaling adhesive; 5, outer needle tube; 6, reflecting ring; 7, inner needle tube; 8, outer conductor; 9, insulating medium; 10, inner conductor; 11, side hole; 12, first welding spot; 13, liquid return cavity; 14, liquid inlet cavity; 15, microwave connector; 16, second welding spot; 17, anti-sticking insulation layer; 18, micropore; 19, third welding spot; 20, anti-sticking layer; 21, developing groove; 22, liquid return pipe; 23, multi-position adjusting switch; and 24, liquid inlet pipe.

DETAILED DESCRIPTION OF THE EMBODIMENTS

The following clearly and completely describes the technical solution in the embodiments of the present disclosure with reference to the embodiments of the present disclosure. Apparently, the described embodiments are merely a part rather than all of the embodiments of the present disclosure. Based on the embodiment in the present disclosure, all other embodiments obtained by the ordinary technical staff in the art under the premise of without contributing creative labor fall within the scope of protection of the present disclosure.

The present disclosure aims to provide a microwave ablation electrode to solve the problems in the prior art. Dual ablation of steam thermal ablation and microwave ablation is realized, the ablation effect is improved, the temperature of the working end of the microwave ablation electrode can be reduced, the wettability of the surrounding tissues at the working end can also be increased, and the carbonization of the lesion tissues is reduced.

To make the foregoing objective, features and advantages of the present disclosure clearer and more comprehensible, the present disclosure is further described in detail below with reference to the attached figures and specific embodiments.

Embodiment I

Figure 1:
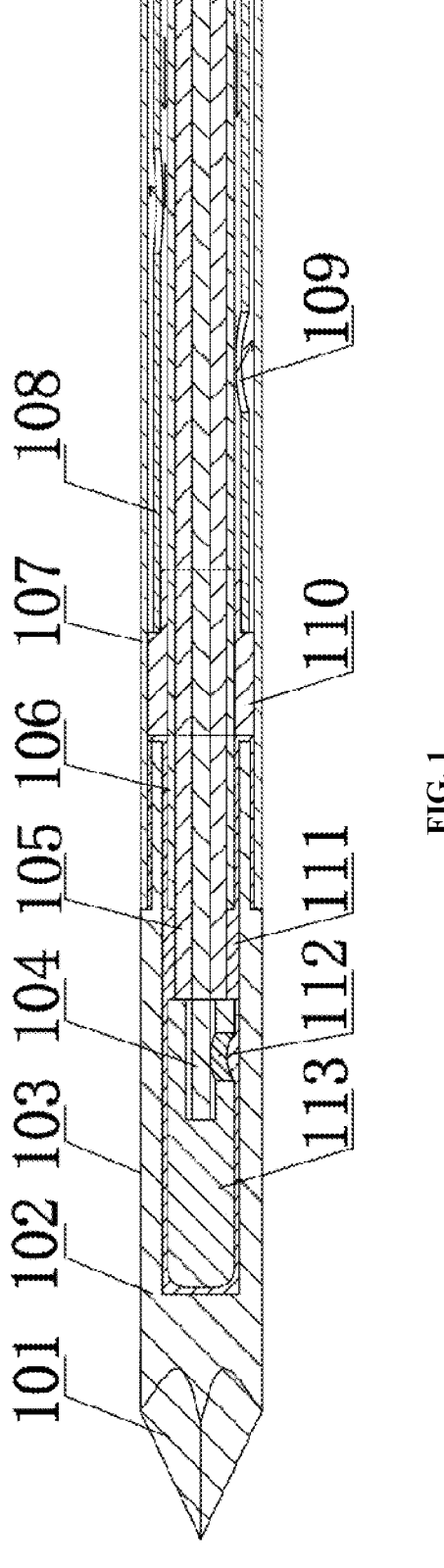
FIG. 1 is a structural schematic diagram of a microwave ablation electrode in the prior art.
Figure 2:
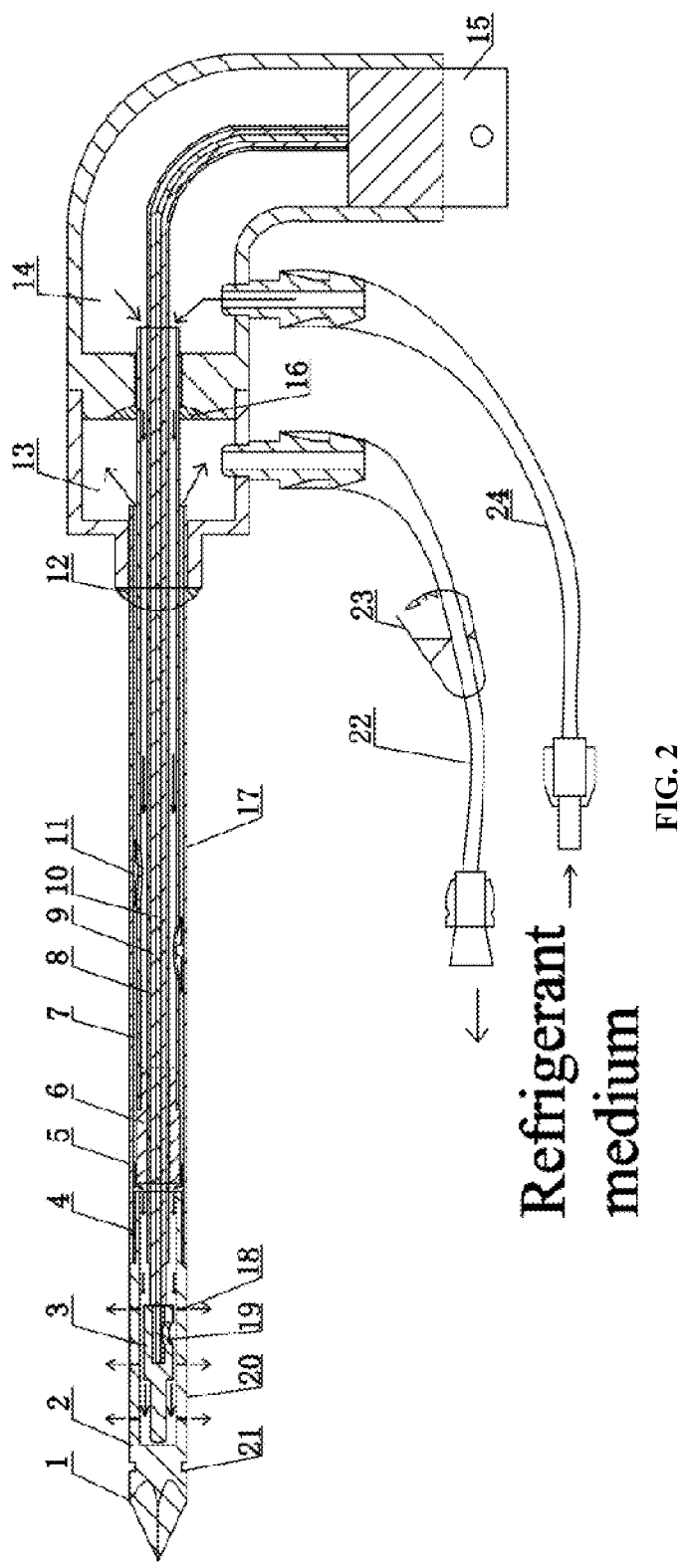
FIG. 2 is a structural schematic diagram of a microwave ablation electrode in an embodiment of the present disclosure.
Figure 3:
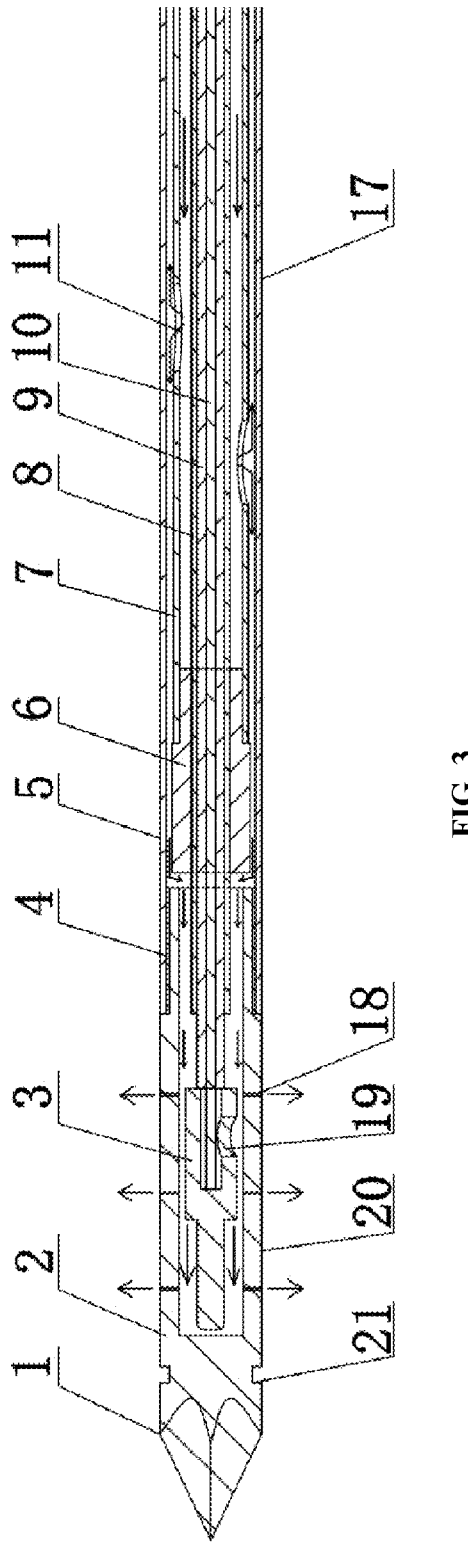
FIG. 3 is a structural schematic diagram of a main needle body in an embodiment of the present disclosure.
Figure 4:
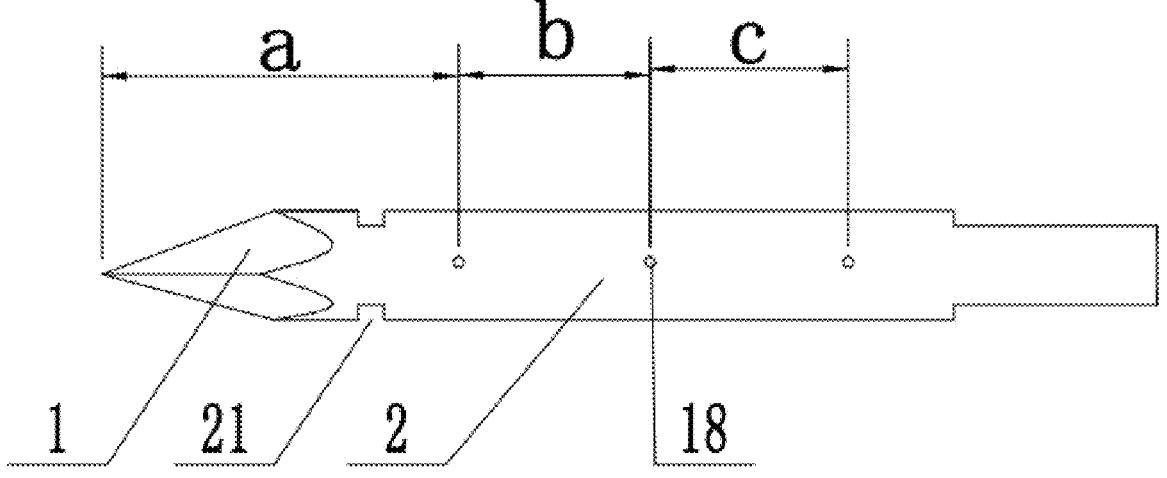
FIG. 4 is a schematic diagram of the arrangement of micropores in an embodiment of the present disclosure.

As shown in FIG. 2 to FIG. 4, the embodiment provides a microwave ablation electrode. The microwave ablation electrode mainly includes a main needle body. A non-working end circulation cooling structure and a working end liquid injection structure are arranged on the main needle body, wherein the non-working end circulation cooling structure can allow a refrigerant medium to reach a front end of a non-working end of the main needle body from a tail end of the non-working end of the main needle body to cool the non-working end of the main needle body and the surrounding tissues, and the non-working end circulation cooling structure can allow the refrigerant medium to flow back. The working end liquid injection structure can allow the refrigerant medium to reach a working end of the main needle body to cool the working end of the main needle body and the surrounding tissues, and can also allow the refrigerant medium to be injected into the lesion tissues to form high-temperature steam, so that steam thermal ablation is realized.

In the embodiment, the non-working end circulation cooling structure is arranged on the main needle body, which can allow the refrigerant medium to cool the non-working end of the main needle body and the surrounding tissues, and can allow the refrigerant medium to flow back, so that high temperature of the non-working end of the main needle body is avoided from scalding normal tissues and damaging a coaxial semi-rigid wire, higher microwave power can be output, and the ablation efficiency is improved.

Furthermore, in the embodiment, the working end liquid injection structure is also arranged on the main needle body and can allow the refrigerant medium to reach the working end of the main needle body to cool the working end part of the main needle body (a working end needle body and a transmitting antenna inside the working end needle body, a front end of the coaxial semi-rigid wire, glue at the bonding place between the working end needle body and an outer needle tube 5) and the surrounding tissues, so that the temperature of the working end of the main needle body can be reduced, and the glue at the bonding place between the working end needle body and the outer needle tube 5 is avoided from being melted at high temperature, causing the working end needle body to fall off. Moreover, in the embodiment, the working end liquid injection structure can also allow the refrigerant medium to be injected into lesion tissues, so that the wettability of the surrounding tissues at the working end can be increased, the temperature of the surrounding tissues at the working end is reduced, the carbonization of the tissues is avoided, the characteristic impedance of the tissues is maintained for a long time, and the injection of microwave energy is facilitated. Therefore, the ablation range is expanded, the ablation shape is more regular, and a near-spherical ablation shape is formed. In addition, after the refrigerant medium enters the lesion tissues, high-temperature steam can be formed through evaporation to realize steam thermal ablation, so that dual ablation of microwave ablation and steam thermal ablation is realized, and the ablation effect is improved.

Further, the working end liquid injection structure can release high-pressure gas inside the working end while liquid is injected, so that the working end needle body is prevented from being broken under the action of high pressure, and the non-working end circulation cooling structure can also release the high-pressure gas.

In the embodiment, the specific structure of the main needle body is similar to the structure of a commonly used microwave ablation needle in the prior art. The main needle body main includes an inner needle tube 7, an outer needle tube 5, a reflecting ring 6, a coaxial semi-rigid wire and a working end needle body. The outer needle tube 5 is sleeved on the inner needle tube 7. The inner needle tube 7 is sleeved on the coaxial semi-rigid wire. The reflecting ring 6 is sleeved on the coaxial semi-rigid wire as well. An inner wall of the reflecting ring 6 is sealed with an outer wall of the coaxial semi-rigid wire, and the reflecting ring 6 can seal a front end of the inner needle tube 7. The working end needle body is arranged at a front end of the outer needle tube 5. A front end of the coaxial semi-rigid wire is electrically connected with a transmitting antenna 3, and a tail end of the coaxial semi-rigid wire can be electrically connected with a microwave ablation host. The transmitting antenna 3 is located in the working end needle body for radiating microwave energy. The reflecting ring 6 and the transmitting antenna 3 are both made of metal material. The coaxial semi-rigid wire includes an inner conductor 10, an insulating medium 9 and an outer conductor 8 arranged in sequence from inside to outside. The inner conductor 10 is used for transmitting microwave energy. A front end of the inner conductor 10 is electrically connected with the transmitting antenna 3 through a third welding spot 19. The insulating medium 9 and the outer conductor 8 are used for shielding microwave energy. The above-mentioned structure is a mature prior art in the art and is not described in detail in the embodiment.

In the embodiment, the transmitting antenna 3 is preferably a T-shaped transmitting antenna, and according to actual needs, a transmitting antenna 3 in other shapes, such as a linear transmitting antenna can also be selected.

In the embodiment, an inner flow channel is formed between an inner wall of the inner needle tube 7 and an outer wall of the coaxial semi-rigid wire. A front end of the inner flow channel is sealed by a tail end face of the reflecting ring 6. The refrigerant medium inside the inner flow channel can reach the front end of the non-working end of the main needle body, namely a tail end of the reflecting ring 6. An outer flow channel is formed between an inner wall of the outer needle tube 5 and an outer wall of the inner needle tube 7. The front end of the inner flow channel communicates with a front end of the outer flow channel, and a tail end of the inner flow channel and a tail end of the outer flow channel communicate with a liquid outlet port and a liquid return port of a liquid supply device, respectively to form the non-working end circulation cooling structure, wherein the refrigerant medium is stored in the liquid supply device, the liquid outlet port is used for providing the refrigerant medium, the liquid return port is used for allowing the refrigerant medium to flow back to the liquid supply device. In the embodiment, the non-working end circulation cooling structure is used for cooling the front end of the non-working end of the main needle body and the surrounding tissues, mainly cooling the coaxial semi-rigid wire, the inner needle tube 7, the outer needle tube 5 and normal tissues around the outer needle tube 5.

In the embodiment, a gap is arranged between an outer wall of the transmitting antenna 3 and an inner wall of the working end needle body, and has a spacing of 0.1 mm to 0.5 mm, preferably. A gap is formed between the front end of the coaxial semi-rigid wire and the inner wall of the working end needle body as well. The two gaps communicate with each other to form a working end flow channel. The working end flow channel communicates with the outer flow channel, so that the refrigerant medium inside the outer flow channel can flow into the working end flow channel. Micropores 18 which allow the refrigerant medium to be injected into the lesion tissues are formed in the working end needle body, and the micropores 18 communicate with the working end flow channel to form the working end liquid injection structure, wherein the micropores 18 are formed in the working end of the main needle body, and the working end is a part, capable of releasing microwave energy, of the main needle body.

In the embodiment, after the refrigerant medium enters the working end flow channel, the refrigerant medium can overflow from the micropores 18. The pore size of the micropores 18 is small, so that only a small amount of the refrigerant medium can overflow from the micropores 18, and the influence on the human body can be reduced as much as possible. Moreover, the small amount of the injected refrigerant medium can be converted into high-temperature steam at high temperature, and the high-temperature steam can be used as an auxiliary ablation medium, so that the ablation range is expanded, and the ablation time shortened. Moreover, the micropores 18, the working end flow channel and the outer flow channel can also release internal pressure generated by high temperature in the working end of the microwave ablation electrode, so that the risk of needle breakage caused by excessive pressure is prevented.

In the embodiment, a tail end of the main needle body is connected with a liquid cavity. A liquid inlet cavity 14 and a liquid return cavity 13 which are separated from each other are formed in the liquid cavity. The tail end of the inner flow channel and the tail end of the outer flow channel communicate with the liquid inlet cavity 14 and the liquid return cavity 13, respectively. The liquid inlet cavity 14 and the liquid return cavity 13 are connected with the liquid outlet port and the liquid return port of the liquid supply device through a liquid inlet pipe 24 and a liquid return pipe 22, respectively. The liquid supply device can be selected according to specific work needs, such as a liquid supply bottle or a liquid supply tank. Specifically, as shown in FIG. 2, a liquid return cavity 13 and a liquid inlet cavity 14 are formed in the liquid cavity from front to back. The liquid return cavity 13 and the liquid inlet cavity 14 are separated by a partition plate. A tail end of the outer needle tube 5 communicates with the liquid return cavity 13. A tail end of the inner needle tube 7 passes through the liquid return cavity 13 and the partition plate in turn and extends into the liquid inlet cavity 14 to realize communication, wherein the inner needle tube 7 is connected with the partition plate through a second welding spot 16.

In the embodiment, a liquid amount adjusting device is installed on the liquid inlet pipe 24 and/or the liquid return pipe 22. The liquid amount adjusting device is used for adjusting the liquid inlet amount or the liquid return amount of the refrigerant medium so as to adjust the injection amount of the refrigerant medium. The liquid amount adjusting device can be selected according to specific work needs, such as a multi-position adjusting switch 23 or a multi-position hose buckle. As a preferred embodiment, in the embodiment, only a liquid amount adjusting device is installed on the liquid return pipe 22 to control the injection amount of the refrigerant medium by controlling the return liquid. If the injection amount of the refrigerant medium is insufficient, the amount of the return liquid is reduced, and the injection amount is increased. If the injection amount is excessive, the amount of the return liquid is increased, and the injection amount is reduced.

In the embodiment, the refrigerant medium is sterile physiological saline, sterile water for injection or liquid medicine, the injection amount of the refrigerant medium is the volume of the refrigerant medium entering into the human body per unit time, and the injection amount of the refrigerant medium is preferably 0.1 ml to 2.0 ml per minute. Moreover, when liquid medicine is used as the refrigerant medium in the embodiment, combined drug treatment can be realized, the healing effect can be improved, the treatment cycle is shortened, and additional drug treatment procedures can be avoided, so that the pain of patients is alleviated.

In the embodiment, side holes 11 are formed in a side face of the front end of the inner needle tube 7, and the inner flow channel communicates with the outer flow channel through the side holes 11. A first gap is arranged between an outer wall of the reflecting ring 6 and an inner wall of the outer needle tube 5, and has a spacing of 0.05 mm to 0.2 mm. A second gap is arranged between a front end face of the reflecting ring 6 and a tail end face of the working end needle body, and has a spacing of 0.1 mm to 1.0 mm, wherein the first gap communicates with the outer flow channel, the second gap communicates with the working end flow channel, and the first gap communicates with the second gap to realize the communication between the working end flow channel and the outer flow channel.

In the embodiment, the flow process of the refrigerant medium is as follows.

The refrigerant medium in the liquid supply device enters into the inner flow channel in the inner needle tube 7 through the liquid inlet pipe 24 and the liquid inlet cavity 14, and then flows out from the side holes 11 in the front end of the inner needle tube 7. A part of the refrigerant medium flows back to the liquid supply device through the outer flow channel, and the other part of the refrigerant medium is injected into the lesion tissues through the gap between the part of the inner needle tube 7 located in front of the side holes 11 and the outer needle tube 5, the first gap, the second gap, the interior of the working end needle body, the working end flow channel and the micropores 18.

In the embodiment, the working end needle body mainly includes a ceramic needle body 2 and a ceramic needle tip 1. A tail end of the ceramic needle body 2 is connected with the front end of the outer needle tube 5 through a sealing adhesive 4. The ceramic needle tip 1 is arranged at a front end of the ceramic needle body 2, wherein the diameter of the tail end of the ceramic needle body 2 is smaller than that of the front end of the outer needle tube 5, and the tail end of the ceramic needle body 2 can extend into the front end of the outer needle tube 5 and is connected through the sealing adhesive 4, so that the connecting strength is improved. The micropores 18 are formed in a working end of the ceramic needle body 2, and the working end of the ceramic needle body 2 is an exposed part, which is not connected with the outer needle tube 5, on the ceramic needle body. Further, the working end needle body can also be a needle body made of other materials, such as an organic glass or polymer plastic needle body.

In the embodiment, as shown in FIG. 4, a circle of micropores 18 is formed in three circumferences of the ceramic needle body 2 with distances of a, a+b and a+b+c from a front end of the ceramic needle tip 1, respectively. Each circle of micropores 18 is uniformly arranged along the circumferential direction, with a total of nine micropores 18. The micropores 18 in each circle are arranged in one-to-one correspondence, and a connecting line of circle centers of the first micropores, a connecting line of circle centers of the second microholes and a connecting line of circle centers of the third micropores in each circle are all parallel to a center line of the outer needle tube 5. Wherein, a is preferably 5 mm to 7 mm, a+b is preferably 8 mm to 10 mm, and a+b+c is preferably 11 mm to 13 mm. The distance between the micropores 18 and the front end of the ceramic needle tip 1, the number of circles of the micropores 18 and the number of the micropores 18 in each circle can be selected according to actual needs.

Further, the micropores 18 may be round micropores 18, square micropores 18, or micropores 18 in other shapes. The number of the micropores 18 in each circle may be the same or different, and the circle centers of the micropores 18 in each circle may be distributed coaxially or in a crossed manner.

In the embodiment, the pore size of each of the micropores 18 is preferably 50 μm to 200 μm, further preferably 50 μm.

In the embodiment, the ceramic needle tip 1 is a triangular needle tip with a sharp blade, and a developing groove 21 is formed in the joint of the ceramic needle tip 1 and the ceramic needle body 2 to form an uneven surface, so that the development is clear under imaging equipment, and side effects caused by repeated positioning puncture, such as pneumothorax, bleeding and tumor implantation, due to wrong puncture or inadequate puncture, are prevented.

In the embodiment, it needs to be explained that the front end is an end close to a tip of the ceramic needle tip 1, and the tail end is an end away from the tip of the ceramic needle tip 1.

In the embodiment, the outer needle tube 5 is made of metal material, and sufficient strength can be ensured at a small diameter, so that the diameter of the main needle body can reach 1.20 mm at least (the diameter of the main needle body can preferably be 1.20 mm to 1.50 mm). The puncture trauma can be reduced during puncture, especially when the outer needle tube 5 is applied to the ablation of small pulmonary nodules, the pneumothorax problem caused by a larger diameter of the microwave ablation electrode can be avoided. It should be noted that the diameter of the main needle body refers to the outer diameter of the main needle body, that is, the outer diameters of the outer needle tube 5 and the ceramic needle body 2.

In the embodiment, the outer needle tube 5 is made of metal material, and an anti-sticking insulation layer 17 is arranged on the outer wall of the outer needle tube 5 to ensure insulation, so that adhesion between the outer needle tube 5 and the surrounding tissues is prevented while insulation is realized. An anti-sticking layer 20 is arranged on an outer wall of the working end needle body to prevent adhesion between the working end needle body and the surrounding tissues. The anti-sticking layer 20 is arranged in a staggered manner with the micropores 18 to prevent the refrigerant medium from flowing out through the micropores 18, and the anti-sticking layer 20 is flush with the anti-sticking insulation layer 17, so that an outer wall of the main needle body becomes a smooth circumferential surface which is convenient for puncture. In the embodiment, the anti-sticking insulation layer 17 and the anti-sticking layer 20 are preferably Teflon coatings which are integrally formed.

In this embodiment, the outer needle tube 5 can be arranged in a grounded shield manner to realize microwave shielding. Specifically, a microwave connector 15 is installed at a tail end of the liquid cavity, and the tail end of the coaxial semi-rigid wire is electrically connected with the microwave ablation host through the microwave connector 15 to realize microwave energy transmission. A shell of the microwave connector 15 can be grounded, the liquid cavity is made of metal material, and the tail end of the outer needle tube 5 is electrically connected with the liquid cavity through the first welding spot 12 and connected with the shell of the microwave connector 15 through the liquid cavity to realize grounding. Alternatively, the outer needle tube 5 can be directly connected to a ground wire to realize grounding. The inner needle tube 7 is made of metal material as well and can be grounded. Specifically, the front end of the inner needle tube 7 is electrically connected with the reflecting ring 6, and the tail end of the inner needle tube 7 is electrically connected with the liquid cavity through the second welding spot 16 and connected with the shell of the microwave connector 15 through the liquid cavity to realize grounding.

In the embodiment, a plastic insulation layer is sleeved on the liquid cavity.

Based on the basic principle of microwave ablation (water can absorb most of microwave energy to generate thermal effect), the water content of the lesion tissues is increased by injecting a small amount of the refrigerant medium, so that the absorption of microwave energy by the lesion tissues is increased, and a thermal effect is converted. The small amount of the injected refrigerant medium can be converted into high-temperature steam at high temperature to realize steam thermal ablation and expand the ablation range. The lesion tissues can also be wetted, the characteristic impedance is maintained, and continuous output of microwave energy is facilitated, so that the ablation range is expanded.

Moreover, the temperatures of the working end and the outer needle tube are reduced through the circulation of the refrigerant medium, so that the temperature of the lesion tissues near the working end and the temperature of the normal tissues around the outer needle tube are reduced, and the carbonization of the lesion tissues and the thermal damage to tissues at the non-treatment parts are prevented. Furthermore, the outer flow channel and the micropores formed in the working end can also be used as channels for the microwave ablation electrode to release high-temperature and high-pressure gas so as to avoid the needle body from being broken at the working end.

In addition to a cold circulation function and a liquid injection function, the microwave ablation electrode of the present disclosure also has the function of adjustable injection flow. Moreover, the microwave ablation electrode is small in diameter and clear in development under imaging equipment, and is a safe and effective microwave ablation electrode which can be applied to diseases such as lung tumors and lung nodules. Moreover, it further should be explained that the present disclosure includes but is not limited to the treatment of lung tumors, nodules and other diseases, and the microwave ablation electrode for other disease sites derived from the principle and structure of the present disclosure can be understood within the protection scope of the present disclosure.

Specific examples are used for illustration of the principles and implementation methods of the present disclosure. The description of the above-mentioned embodiments is used to help illustrate the method and its core principles of the present disclosure. In addition, those skilled in the art can make various modifications in terms of specific embodiments and scope of application in accordance with the teachings of the present disclosure. In summary, the contents of this specification should not be understood as the limitation of the present disclosure.

What is claimed is:

1. A microwave ablation electrode, comprising a main needle body, a working end of the main needle body is capable of releasing microwave energy to realize microwave ablation; a non-working end circulation cooling structure and a working end liquid injection structure are arranged on the main needle body, wherein;

the non-working end circulation cooling structure is capable of allowing a refrigerant medium to reach a front end of a non-working end of the main needle body to cool the non-working end of the main needle body and surrounding tissues, and the non-working end circulation cooling structure is capable of allowing the refrigerant medium to flow back;

the working end liquid injection structure is capable of allowing the refrigerant medium to reach the working end of the main needle body to cool the working end and the surrounding tissues, and is also capable of allowing the refrigerant medium to be injected into lesion tissues and absorb microwave energy to form steam, so that steam thermal ablation is realized;

the main needle body comprises an inner needle tube, an outer needle tube, a reflecting ring, a coaxial semi-rigid wire and a working end needle body, the outer needle tube is sleeved on the inner needle tube, the inner needle tube is sleeved on the coaxial semi-rigid wire, the reflecting ring is sleeved on the coaxial semi-rigid wire, an inner wall of the reflecting ring is sealed with an outer wall of the coaxial semi-rigid wire, the reflecting ring is capable of sealing a front end of the inner needle tube, and the working end needle body is arranged at a front end of the outer needle tube; a front end of the coaxial semi-rigid wire is electrically connected with a transmitting antenna, a tail end of the coaxial semi-rigid wire is capable of being electrically connected with a microwave ablation host, and the transmitting antenna is located in the working end needle body;

communicating gaps are arranged between the transmitting antenna and an inner wall of the working end needle body and between the front end of the coaxial semi-rigid wire and the inner wall of the working end needle body to form a working end flow channel, the working end flow channel communicates with the non-working end circulation cooling structure, micropores which allow the refrigerant medium to be injected into the lesion tissues are formed in the working end needle body, and the micropores communicate with the working end flow channel to form the working end liquid injection structure;

an inner flow channel is formed between the inner needle tube and the coaxial semi-rigid wire, an outer flow channel is formed between the outer needle tube and the inner needle tube, a front end of the inner flow channel communicates with a front end of the outer flow channel, and a tail end of the inner flow channel and a tail end of the outer flow channel communicate with a liquid outlet port and a liquid return port of a liquid supply device, respectively to form the non-working end circulation cooling structure, the liquid supply device is capable of providing the refrigerant medium, and the outer flow channel communicates with the working end flow channel;

a first gap is arranged between an outer wall of the reflecting ring and an inner wall of the outer needle tube, and a second gap is arranged between a front end face of the reflecting ring and a tail end face of the working end needle body, the first gap communicates with the outer flow channel, the second gap communicates with the working end flow channel, and the first gap communicates with the second gap to realize the communication between the working end flow channel and the outer flow channel;

the first gap has a spacing of 0.05 mm to 0.2 mm, and the second gap has a spacing of 0.1 mm to 1.0 mm; and each of the micropores has a pore size of 50 μm to 200 μm.

2. The microwave ablation electrode according to claim 1, wherein a tail end of the main needle body is connected with a liquid cavity, a liquid inlet cavity and a liquid return cavity which are separated from each other are formed in the liquid cavity, and the tail end of the inner flow channel and the tail end of the outer flow channel communicate with the liquid inlet cavity and the liquid return cavity, respectively; and the liquid inlet cavity and the liquid return cavity are connected with the liquid outlet port and the liquid return port of the liquid supply device through a liquid inlet pipe and a liquid return pipe, respectively.

3. The microwave ablation electrode according to claim 2, wherein a liquid amount adjusting device is installed on the liquid inlet pipe and/or the liquid return pipe, and the liquid amount adjusting device is used for adjusting a liquid inlet amount or a liquid return amount of the refrigerant medium so as to adjust the injection amount of the refrigerant medium; and the injection amount of the refrigerant medium is a volume of the refrigerant medium entering the human body per unit time.

4. The microwave ablation electrode according to claim 1, wherein the outer needle tube is made of metal material, the outer needle tube is capable of being arranged in a grounded shield manner, and an anti-sticking insulation layer is arranged on an outer wall of the outer needle tube; and an anti-sticking layer is arranged on an outer wall of the working end needle body, the anti-sticking layer is arranged in a staggered manner with the micropores, and the anti-sticking layer is flush with the anti-sticking insulation layer.

5. The microwave ablation electrode according to claim 4, wherein the main needle body has a minimum diameter of 1.20 mm.

6. The microwave ablation electrode according to claim 1, wherein the working end needle body comprises a ceramic needle body and a ceramic needle tip, a tail end of the ceramic needle body is connected with the front end of the outer needle tube, the ceramic needle tip is arranged at a front end of the ceramic needle body, wherein the micropores are formed in the ceramic needle body, and a developing groove is formed in the ceramic needle tip.

\* \* \* \* \*